United States Patent [19]

Distler et al.

[11] 3,948,978

[45] Apr. 6, 1976

[54] PRODUCTION OF GLYCOL MONOESTERS OF α, β-UNSATURATED CARBOXYLIC ACIDS

[75] Inventors: Harry Distler, Ludwigshafen; Kurt Schneider, Bad Duerkheim, both of Germany

[73] Assignee: BASF Aktiengesellschaft, Ludwigshafen (Rhine), Germany

[22] Filed: Dec. 4, 1974

[21] Appl. No.: 529,346

[30] Foreign Application Priority Data
Dec. 13, 1973 Germany............................ 2361907

[52] U.S. Cl............................. 260/486 B; 260/486 H
[51] Int. Cl.²........................................ C07C 69/54
[58] Field of Search ................................ 260/486 B

[56] References Cited
UNITED STATES PATENTS

| | | | |
|---|---|---|---|
| 3,174,995 | 3/1965 | Cour | 260/486 B |
| 3,494,605 | 2/1970 | Rehfuss | 260/486 B |
| 3,652,647 | 3/1972 | Zey | 260/486 B |

*Primary Examiner*—Lorraine A. Weinberger
*Assistant Examiner*—P. Killos
*Attorney, Agent, or Firm*—Johnston, Keil, Thompson & Shurtleff

[57] ABSTRACT

The production of glycol monoesters of α,β-unsaturated carboxylic acids of three or four carbon atoms and 1,2-diols of two to four carbon atoms by the reaction of acids with 1,2-alkylene oxides of two to four carbon atoms at elevated temperature in the presence of catalysts and polymerization initiators and also of molecular oxygen as an additional agent for suppressing polymerization.

14 Claims, No Drawings

PRODUCTION OF GLYCOL MONOESTERS OF ALPHA, BETA-UNSATURATED CARBOXYLIC ACIDS

This invention relates to a process for the production of glycol monoesters of α, β-unsaturated carboxylic acids of three or four carbon atoms and 1,2-diols of two to four carbon atoms by the reaction of an α,β-unsaturated carboxylic acid of three or four carbon atoms with a 1,2-alkylene oxide of two to four carbon atoms in the presence of a catalyst at elevated temperature and in the presence of a polymerization inhibitor.

It is known from German Pat. Nos. 1,257,776 and 1,248,660 that the corresponding glycol monoesters can be obtained in a simple manner by the reaction of acrylic acid with an alkylene oxide in the presence of a catalyst. Even when polymerization inhibitors are used it is not possible however to exclude polymerization of the starting materials or the products prepared. The said polymerization results not only in loss of yield but for reasons not yet understood polymerization takes place preferentially at the points of introduction for the alkylene oxide and this results in stoppages and involves the whole reaction mixture in a manner which is not reproducible so that finally the reaction mixture becomes completely useless and can only be removed at great expense from the apparatus used.

It is an object of the invention to suppress polymerization of the reactants in the reaction of an α,β-unsaturated carboxylic acid with a 1,2-alkylene oxide.

We have found that glycol monoesters of α,β-unsaturated carboxylic acids of three or four carbon atoms and 1,2-diols of two to four carbon atoms can be obtained more advantageously by the reaction of an α,β-unsaturated carboxylic acid of three or four carbon atoms and a 1,2-alkylene oxide of two to four carbon atoms at elevated temperature in the presence of a catalyst and a polymerization inhibitor, when molecular oxygen or a gas containing the same is used in addition to the polymerization inhibitor.

The new process has the advantage that the tendency to polymerize can be suppressed to a minimum in a simple manner. In particular the new process has the advantage that uncontrolled polymerization starting at the points of introduction for alkylene oxide no longer takes place. The new process also has the advantage that polymerization no longer takes place at points outside the reaction mixture, for example in the gas space above the reaction mixture.

The new process is remarkable because hitherto the presence of molecular oxygen has been very carefully avoided when using an alkylene oxide.

An α,β-unsaturated carboxylic acid of three or four carbon atoms is used as starting material. Acrylic acid and methacrylic acid have achieved particular industrial importance.

The α,β-alkylene oxides used are those of two to four carbon atoms. They may contain chlorine as a substituent as in the case of epichlorohydrin. Preferred 1,2-alkylene oxides have two or three carbon atoms. Ethylene oxide has achieved particular importance. Examples of other suitable alkylene oxides are propylene oxide, epichlorohydrin and 1,2-butylene oxide.

The α,β-unsaturated carboxylic acid and the 1,2-alkylene oxide are as a rule used in a molar ratio of from 1:1 to 1:10. It is particularly advantageous to use from 1 to 1.5 moles of 1,2-alkylene oxide per mole of carboxylic acid.

The reaction is carried out at elevated temperature and generally at from 25° to 200°C. Particularly good results are obtained at temperatures of from 60° to 150°C. The reaction is generally carried out at atmospheric pressure. It is also convenient to use superatmospheric pressure, for example of up to 20 atmospheres, particularly when a starting material is used which has a low boiling point.

The reaction is carried out in the presence of a catalyst. Suitable catalysts include Lewis acids such as boron trifluoride etherate, amine oxides such as dimethyllaurylamine oxide, phosphines such as triphenyl phosphine, betaines such as trimethylaminoacetic acid and taurine, carboxamides and hydrazides of carboxylic acids of up to eighteen carbon atoms and particularly dimethylformamide and urea, and also phosphoric acid amides such as hexamethylphosphoric acid triamide. Other suitable catalysts include sulfoxides and thioethers and sulfonium salts which may contain aliphatic, cycloaliphatic, araliphatic or aromatic hydrocarbon radicals of up to sixteen carbon atoms and these radicals may be identical or different. They may also together form members of a ring which preferably has five or six members. They may each contain a substituent, for example a hydroxyl group or a carboxyl group. Examples of suitable compounds are dimethyl sulfide, diethyl sulfide, methylphenyl sulfide, thiodiacetic acid, thiodibutyric acid, thiodiglycol and thioxane. The thio or thioether grouping may be present more than once in the molecule as in the compounds: 3,9-dithio-6-oxa-undecanediol-1,11 and 3,6-dithiooctanediol-1,8. An example of a suitable sulfonium salt is tris-β-oxyethyl-sulfonium hydrochloride. Examples of suitable sulfoxides are dimethyl sulfoxide, diethyl sulfoxide, methylethyl sulfoxide, tetramethylene sulfoxide, diphenyl sulfoxide and methylphenyl sulfoxide.

Thioethers and sulfoxides and also phosphines, for example triphenyl phosphine, have achieved particular industrial importance as catalysts.

It is advantageous to use the catalyst in an amount of from 0.1 to 20% and particularly from 1 to 10% by weight based on the starting materials.

The reaction is furthermore carried out in the presence of a polymerization inhibitor. Examples of suitable polymerization inhibitors are nitroso compounds such as nitrosodiphenylamine and isoacrylonitrite, salts of N-nitrosocyclohexylhydroxylamine and also methylene blue, thiodiphenylamine and phenothiazine. Hydroquinone and hydroquinone monomethyl ether are particularly preferred as inhibitors. The inhibitors are usually used in amounts of from 10 to 1000 ppm based on the α,β-unsaturated carboxylic acid used. Amounts of from 100 to 500 ppm are particularly preferred.

The essential feature of the invention is that molecular oxygen, employed as pure oxygen or as a gas containing the same, is used additionally during the reaction. Suitable gas containing oxygen may for example contain from 15 to 25% by volume of oxygen. Air has acquired particular significance. It is preferred to maintain in the reaction mixture a content of molecular oxygen which is below the explosion range of the particular alkylene oxide used. For example when propylene oxide is used the oxygen content is less than the explosion limit of 14% by volume.

From 100 to 1000 ppm by volume of oxygen in the reaction mixture is as a rule sufficient.

The glycol monoesters of α,β-unsaturated carboxylic acids produced according to the process of the invention are used as a rule in the form in which they are obtained. They are suitable as crosslinking agents in the production of surface coatings and vinyl polymers.

The process according to the invention is illustrated in the following Examples. The parts given in the Examples are by weight. They bear the same relation to parts by volume as the kilogram to the liter.

EXAMPLE 1

5 parts of thiodiglycol is placed in a dry glass-lined vessel having a capacity of 1000 parts by volume. The vessel is then closed and filled with 504 parts of acrylic acid (stabilized with 500 ppm of hydroquinone monomethyl ether). After the pressure of the vessel has been tested it is heated to 75°C and is supplied with about 35 parts per hour of propylene oxide while metering in 3 parts by volume per hour of air. The pressure should not exceed 2.8 atmospheres gauge. After about 90% of the propylene oxide has been introduced another 5 parts of thiodiglycol containing 0.127 part of hydroquinone monomethyl ether is added.

After the whole amount of 430 parts of propylene oxide has been introduced reaction is allowed to proceed for another three hours. The content of acrylic acid is determined by sample titration. At an acrylic acid content of more than 1% reaction is allowed to proceed with an appropriate addition of propylene oxide. At an acrylic acid content of less than 1% acrylic acid is added to restore it to 1%.

Excess propylene oxide is removed at 50°C in vacuo. The contents of the vessel are cooled to about 20°C and the vessel is aerated and emptied out. About 900 parts of hydroxypropyl acrylate is obtained which contains less than 0.1% by weight of polymers.

EXAMPLE 2

4.5 parts of thiodiglycol is placed in a dry glass-lined vessel having a capacity of 1000 parts by volume. The vessel is closed and filled with 472 parts of acrylic acid stabilized with 500 ppm of hydroquinone monomethyl ether. After a pressure test the whole is heated to 75°C and a total of 242 parts of ethylene oxide is slowly introduced while passing air in at the rate of about 3 parts by volume per hour. When about 90% of the ethylene oxide has been introduced, another 4.5 parts of thiodiglycol and 0.140 parts of hydroquinone monomethyl ether are added. Reaction is allowed to proceed for another five hours and the acrylic acid content is determined by a sample titration. When the content of acrylic acid rises above 10% the appropriate amount of ethylene oxide is introduced. When the content of acrylic acid falls below 10% it is restored to 10% with acrylic acid.

The excess ethylene oxide is removed in vacuo at 40°C. The whole is aerated and the product discharged. 700 parts of β-hydroxyethyl acrylate is obtained which contains less than 0.1% by weight of polymer.

EXAMPLE 3

5 parts of thiodiglycol is placed in a dry glass-lined vessel. The vessel is closed and filled with 516 parts of methacrylic acid which has been stabilized with 500 ppm of hydroquinone monomethyl ether. After a pressure test the vessel is heated to 75°C and introduction of 370 parts of propylene oxide is commenced while passing in air at the rate of 3 parts by volume per hour. The pressure in the vessel should not exceed 2.8 atmospheres gauge. When about 90% of the propylene oxide has been introduced another 5 parts of thiodiglycol catalyst and 0.127 part of hydroquinone monomethyl ether are added. Reaction is allowed to proceed for another three hours.

The methacrylic acid content is tested by sample titration. If the content of methacrylic acid should rise above 1% an appropriate amount of propylene oxide is passed in. If the content of methacrylic acid falls below 1% it has to be restored to 1% with methacrylic acid. The excess propylene oxide is withdrawn by suction at 50°C. The whole is cooled, aerated and discharged. 860 parts of hydroxypropyl methacrylate is obtained which contains less than 0.1% by weight of polymers.

Comparative Example I 5 parts of thiodiglycol is placed in a dry glass-lined vessel having a capacity of 1000 parts by volume. The vessel is then closed and filled with unstabilized acrylic acid. After the vessel has been pressure-tested it is heated to 75°C and about 35 parts of propylene oxide is introduced per hour while bubbling in air at 3 parts by volume per hour. The pressure in the vessel should not exceed 2.8 atmospheres gauge.

After about 90% of the propylene oxide has been introduced another 5 parts of thiodiglycol is added.

After the total amount of 430 parts of propylene oxide has been introduced spontaneous polymerization takes place so that the contents of the vessel solidify.

Comparative Example II 5 parts of thiodiglycol is placed in a dry glass-lined vessel having a capacity of 1000 parts by weight and as described in Example 1 504 parts of acrylic acid (stabilized with 500 ppm of hydroquinone monomethyl ether) is reacted with 430 parts of propylene oxide without adding oxygen in the form of air. Spontaneous polymerization takes place during the afterreaction, as in Example I.

Comparative Example III

As described in Example II 504 parts of acrylic acid (stabilized with 500 ppm of hydroquinone and 500 ppm of hydroquinone monomethyl ether) is reacted with 430 parts of propylene oxide at 75°C without atmospheric oxygen.

In this case also, as in Example II, spontaneous polymerization takes place during afterreaction.

We claim:

1. A process for the production of glycol monoester of an α,β-unsaturated carboxylic acid of three or four carbon atoms and a 1,3-diol of two to four carbon atoms by the reaction of an α,β-unsaturated carboxylic acid of three or four carbon atoms and a 1,2-alkylene oxide of two to four carbon atoms at elevated temperature in the presence of a catalyst and a polymerization inhibitor, wherein molecular oxygen or a gas containing the same is added to the reaction mixture in an amount providing up to 1000 ppm of molecular oxygen in the reaction mixture.

2. A process as claimed in claim 1 wherein the content of the molecular oxygen used in the reaction mixture is below the explosion limit of the specific alkylene oxide used.

3. A process as claimed in claim 1 wherein the polymerization inhibitor used is hydroquinone or hydroquinone monomethyl ether.

4. A process as claimed in claim 1 wherein the α,β-unsaturated carboxylic acid used is acrylic acid or methacrylic acid.

5. A process as claimed in claim 1 wherein the 1,2-alkylene oxide used is ethylene oxide, propylene oxide, epichlorohydrin or 1,2-butylene oxide.

6. A process as claimed in claim 1 wherein the molar ratio of α,β-unsaturaated carboxylic acid to 1,2-alkylene oxide is from 1:1 to 1:10.

7. A process as claimed in claim 6 wherein the said molar ratio is from 1:1 to 1:1.5.

8. A process as claimed in claim 1 carried out at a temperature of from 25° to 200°C.

9. A process as claimed in claim 1 carried out at a temperature of from 60°C to 150°C.

10. A process as claimed in claim 1 carried out at atmospheric pressure.

11. A process as claimed in claim 1 carried out at a pressure of up to 20 atmospheres.

12. A process as claimed in claim 1 wherein the catalyst used is a thioether or sulfoxide.

13. A process as claimed in claim 1 wherein the catalyst used is a phosphine.

14. A process as claimed in claim 1 wherein from 100 to 1000 ppm by volume of molecular oxygen is employed in the reaction mixture.

\* \* \* \* \*